(12) United States Patent
Madsen et al.

(10) Patent No.: US 10,399,276 B2
(45) Date of Patent: Sep. 3, 2019

(54) SYSTEM AND METHOD FOR CONTROLLING AT LEAST ONE VARIABLE DURING LAYUP OF A COMPOSITE PART USING AUTOMATED FIBER PLACEMENT

(71) Applicant: General Electric Company, Schenectady, NY (US)

(72) Inventors: Christopher James Madsen, Bountiful, UT (US); Ram Kumar Upadhyay, Niskayuna, NY (US); Stefaan Guido Van Nieuwenhove, Hohenkammer (DE); Thomas Kluge, Lenggries (DE); Mathias Ernst Messmer, Lenggries (DE); Martin Petersen, Poing (DE)

(73) Assignee: General Electric Company, Schenectady, NY (US)

( * ) Notice: Subject to any disclaimer, the term of this patent is extended or adjusted under 35 U.S.C. 154(b) by 393 days.

(21) Appl. No.: 14/824,348

(22) Filed: Aug. 12, 2015

(65) Prior Publication Data

US 2017/0043539 A1   Feb. 16, 2017

(51) Int. Cl.
*B32B 41/00* (2006.01)
*B29C 65/00* (2006.01)
(Continued)

(52) U.S. Cl.
CPC ............ *B29C 66/01* (2013.01); *B29C 70/382* (2013.01); *B29C 70/384* (2013.01);
(Continued)

(58) Field of Classification Search
CPC ..... B29C 66/01; B29C 70/384; B29C 70/388; B29C 70/386; G01N 2021/8472; G01N 21/8422
(Continued)

(56) References Cited

U.S. PATENT DOCUMENTS 8,037,843 B2   10/2011   Vermilyea et al.
8,377,239 B2   2/2013    Engelbart et al.
(Continued)

FOREIGN PATENT DOCUMENTS

CA   2 575 189 A1   7/2007
CA   2 853 845 A1   1/2015
(Continued)

OTHER PUBLICATIONS

Lukaszewicz et al.,"The engineering aspects of automated prepreg layup: History, present and future", Composites Part B: Engineering, ScienceDirect, vol. 43, Issue: 3, pp. 997-1009, Apr. 2012.
(Continued)

*Primary Examiner* — Michael N Orlando
*Assistant Examiner* — Joshel Rivera
(74) *Attorney, Agent, or Firm* — Joseph Christian (57) ABSTRACT

An automated in-line feed-through system and method, integrates the ability to control one or more variables during part fabrication with the layup of one or more fiber tows to form a composite part. The system includes an automated layup system configured to receive a feed-through of one or more fiber tows as an input material. The automated in-line feed-through system further includes a controller configured to respond to measurement data obtained by one or more samplings of the input material and/or a plurality of laid up plies that form a laminate. The controller in response to the obtained measurement data provides adjustment of the feed-through of the one or more fiber tows to compensate for a variation in one or more of the weights from a reference weight.

18 Claims, 5 Drawing Sheets

(51) Int. Cl.
*B29C 70/38* (2006.01)
*G01N 21/84* (2006.01)

(52) U.S. Cl.
CPC .......... *B29C 70/386* (2013.01); *B29C 70/388* (2013.01); *G01N 21/8422* (2013.01); *G01N 2021/8472* (2013.01)

(58) Field of Classification Search
USPC .......................... 156/64, 350, 351, 378, 379
See application file for complete search history.

(56) References Cited

U.S. PATENT DOCUMENTS

| | | | |
|---|---|---|---|
| 8,714,226 | B2 | 5/2014 | Senibi et al. |
| 2005/0039843 | A1 | 2/2005 | Johnson et al. |
| 2007/0173966 | A1 | 7/2007 | Oldani |
| 2009/0211698 | A1 | 8/2009 | McCowin |
| 2010/0006205 | A1 | 1/2010 | McCowin et al. |
| 2012/0073726 | A1 | 3/2012 | Koeniger et al. |
| 2012/0325398 | A1 * | 12/2012 | Silcock ................ B29C 70/386 156/176 |
| 2013/0199718 | A1 | 8/2013 | Ralfs et al. |
| 2014/0154496 | A1 | 6/2014 | Sang et al. |
| 2014/0370237 | A1 | 12/2014 | Ponsolle et al. |
| 2015/0030803 | A1 | 1/2015 | Butler et al. |

FOREIGN PATENT DOCUMENTS

| | | | |
|---|---|---|---|
| CN | 104011538 | A | 8/2014 |
| EP | 1 810 816 | A2 | 7/2007 |
| EP | 2842867 | A1 | 3/2015 |
| JP | H04-82729 | A | 3/1992 |
| JP | 2009-166503 | A | 7/2009 |
| JP | 2011-515242 | A | 5/2011 |
| JP | 2011-527648 | A | 11/2011 |
| JP | 2015-016691 | A | 1/2015 |
| JP | 2016-525471 | A | 8/2016 |
| WO | 99/22932 | A1 | 5/1999 |
| WO | 2012046021 | A1 | 4/2012 |
| WO | WO-2013093071 | A1 * | 6/2013 ............. G01N 27/90 |
| WO | 2014/153535 | A2 | 9/2014 |
| WO | 2014147243 | A1 | 9/2014 |

OTHER PUBLICATIONS

Extended European Search Report and Opinion issued in connection with corresponding EP Application No. 16183108.6 dated Mar. 31, 2017.

Machine Translation and Notification of Reasons for Refusal issued in connection with corresponding JP Application No. 2016-151634 dated Sep. 26, 2017.

First Office Action and Search issued in connection with corresponding CN Application No. 201610659512.8 dated Mar. 15, 2018.

* cited by examiner

SYSTEM AND METHOD FOR CONTROLLING AT LEAST ONE VARIABLE DURING LAYUP OF A COMPOSITE PART USING AUTOMATED FIBER PLACEMENT

BACKGROUND

The disclosure relates generally to automated fiber placement systems and methods and, more particularly, to a system and method for controlling one or more variables during fabrication of composite parts using automated fiber placement.

With the introduction of automated layup process, such as Automated Fiber Placement (AFP) and Automated Tape Laying (ATL), an automated and more cost effective method of producing composite parts may be utilized. Yet, in large rotating components such as composite fan blades found in gas turbine engines, in which tip speeds may reach speeds close to the speed of sound, any variation in external shape and between neighboring blades as a result of manufacturing variances using these automated layup processes, may have a large impact on noise and aerodynamic losses leading to higher fuel consumption. As an example, for fan blade manufacturing, in order to make a conforming fan blade, it must have the correct thickness to meet aerodynamic requirements. In addition, the correct weight is required so that the blade set for an engine can be balanced. Improved weight and thickness control reduces scrap and improves first pass yield. In addition, by matching a set of blades in an engine with regard to overall component thickness and weight, significant improvement in fuel efficiency may be realized, resulting in reduced engine noise.

Current manufacturing processes, such as used during a blade manufacture process, typically involve a raw carbon fiber prepreg, supplied by a material vendor that has significantly larger variation in weight than the finished part specification. Accordingly, a process is needed to reduce variation during fabrication so that it is not seen in the final product.

It would therefore be desirable to provide a novel system and method of fabrication using an automated layup process that provides for control of one or more variables, such as weight and/or thickness, of the resultant composite part during the automated layup process.

BRIEF DESCRIPTION

These and other shortcomings of the prior art are addressed by the present disclosure, which includes an automated in-line manufacturing system and a method for controlling the thickness and weight of a composite part manufactured using the automated in-line manufacturing system.

Briefly, one aspect of the present disclosure resides in an automated in-line manufacturing system for controlling at least one variable during layup of a composite part using automated fiber placement. The automated in-line manufacturing system including an automated layup system and a controller. The automated layup system is configured to receive a feed-through of one or more fiber tows as an input material and provide layup of the one or more fiber tows to form a laminate of one or more laid up plies. The controller is configured to respond to measurement data obtained in one or more samplings and adjust a layup program of the one or more fiber tows to compensate for a variation from one or more of a reference weight of the input material and a reference weight of the laminate.

Another aspect of the disclosure resides in an automated in-line manufacturing system for controlling at least one of a thickness and a weight of a composite part manufactured with the automated in-line manufacturing system. The automated in-line manufacturing system including an automated layup system and a controller. The automated layup system is configured to receive a feed-through of one or more fiber tows as an input material and provide layup of the one or more fiber tows to form a laminate of one or more laid up plies. The controller is configured to adjust at least one of a fiber tow length, and a change in a number of plies being laid up using feedback based on measurement data obtained in one or more samplings to compensate for a variation from one or more of a reference weight of the input material and a reference weight of the laminate.

Yet another aspect of the disclosure resides in a method for controlling the thickness and weight of a composite part manufactured using an automated in-line manufacturing system. The method including: (a) laying up one or more fiber tows using an automated layup system to form a laminate of one or more laid up plies, the laying up process including adhering the one or more fiber tows to a surface of a substrate to form the laminate, the automated layup system configured to receive a feed-through of the one or more fiber tows as an input material; (b) obtaining measurement data in one or more samplings during the laying up of the one or more fiber tows; (c) responding to the measurement data to adjust the layup program of the one or more fiber tows to compensate for a variation from one or more of a reference weight of the input material and a reference weight of the laminate; and (d) repeating steps (a)-(c) until layup of the one or more fiber tows is complete.

Various refinements of the features noted above exist in relation to the various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of the present disclosure without limitation to the claimed subject matter.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
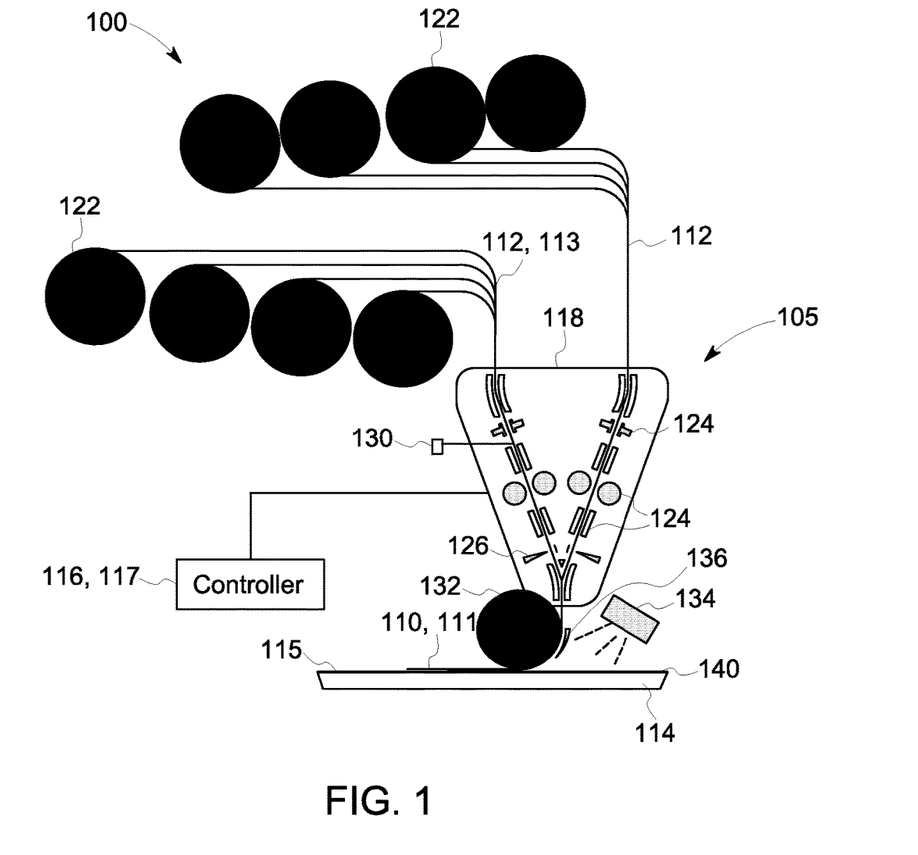
FIG. 1 schematically depicts in side view, an automated in-line manufacturing system for controlling at least one variable during layup of a composite part, in accordance with one or more embodiments shown or described herein.

A composite automated in-line manufacturing system 100, including an automated in-line layup system 105 and a controller 116 is disclosed for the layup of one or more fiber tows 112, as an input, or parent, material 113, to form a composite part 140, as described generally with reference to FIG. 1. The automated in-line manufacturing system 100 can be used for controlling the thickness and weight of a composite part 140, non-limiting examples of which include low weight, high strength aircraft and automotive parts. More specifically, FIG. 1 is a diagrammatic illustration of one embodiment of the automated in-line manufacturing system 100 in accordance with aspects of the present disclosure for layup of the one or more fiber tows 112, such as on to a substrate 114, to form a laminate 110 of one or more laid up plies 111. As used herein, the term "substrate" may include a film, a mold, a tool, or the like used for fabrication of a composite part. The substrate 114 may be manually or automatically placed in the automated in-line manufacturing system 100 in a desired location. The substrate may be operably provided with indicia, pins, or other suitable means for use in determining and/or aligning the substrate 114 relative to the automated in-line manufacturing system 100. In one embodiment, the automated in-line manufacturing system 100 may utilize pre-pregs, whereby the one or more fiber tows 112 are pre-impregnated with a resin system. In an alternate embodiment, the automated in-line manufacturing system 100 may utilize dry fiber tows and include a means for delivering a resin, as described below. The automated in-line manufacturing system 100 further comprises the controller 116, such as a computing unit or computer, operable for controlling the automated in-line manufacturing system 100, and more particularly a layup program 117.

For the example arrangement shown in FIG. 1, the composite automated in-line manufacturing system 100 includes a fiber dispensing means 118 for feeding the one or more fiber tows 112, where each of the one or more fiber tows 112 is moving at a respective fiber speed. As previously indicated, in this particular embodiment, the one or more fiber tows 112 are pre-impregnated with a resin, and commonly referred to as pre-pregs. The fiber dispensing means 118 may be configured to separately feed each of the one or more fiber tows 112, such that the tows 112 can be fed at different rates or at the same rate, depending upon design parameters and in response to the controller 116 and the layup program 117. In one non-limiting example, the fiber dispensing means 118 is in communication with one or more spools 122 onto which each of the tows in the one or more tows 112 is initially wound on a respective one of the spools 122.

In an embodiment the one or more fiber tows 112 comprise any suitable reinforcing material, for example, relatively continuous fibers, or tows, may be arranged to form a unidirectional array of fibers. Useful fibers to be included in such reinforcing materials, such as tapes, or fabrics, include without limitation, glass fibers, carbon and graphite fibers, basalt fibers, polymeric fibers, including aramide and boron filaments, silica fibers, copper fibers and the like. The fibers may be non-conductive or conductive, depending upon the desired application of the composite fiber. In this particular non-limiting example, the one or more fiber tows 112 comprise carbon fibers. However, the disclosure is not limited to these specific fiber types.

As indicated in FIG. 1, the composite automated in-line manufacturing system 100 further includes the controller 116. The controller 116 is configured to respond to obtained measurement data (described presently) to provide adjustments to the automated in-line manufacturing system 100 based on a calculated required compensation. In an embodiment, measurement data may include one or more samplings of at least one of a weight of the input material 113, and more particularly the one or more fiber tows 112, and/or a weight of the laminate 110 during fabrication, and more particularly during buildup of the plies 111, that form the composite part 140. The controller 116 is configured to adjust the layup program 117 and more particularly the feed-through of the one or more fiber tows 112, in response to the measurement data, to compensate for a variation from a reference weight of the input material 113 or laminate 110 during build. More particularly, based on the variance of the measurement data from the reference data, the controller 116, and more particularly a layup program 117 that is controlling the automated in-line manufacturing system 100, is adjusted to compensate for the variation during build. Such adjustments may include, but are not limited to, one or more of a change in the number of plies being laid up to form the laminate 110 and/or a change in a length of the one or more fiber tows 112 within the automated in-line manufacturing system 100 using feedback based on measurement data of the one or more samplings.

To provide for the measurement data, the composite automated in-line manufacturing system 100 may include one or more sensors 130 for inline monitoring/sampling at least one of a weight of the input material 113, and more particularly the one or more fiber tows 112, and/or a weight of the laminate 110 during build. Although a single sensor 130 is indicated in FIG. 1, a plurality of sensor 130 may be employed, and in one non-limiting example, one sensor 130 is provided for each of the fiber tows 112. Example sensors include optical or contact sensors.

The controller 116 may exchange information with the automated in-line manufacturing system 100 as indicated in FIG. 1, to optimize the fabrication of the laminate 110 and thus the final composite part 140. The controller 116 may be configured to adjust the number of plies 111 being laid up in the laminate 110 and/or a change a length of the one or more fiber tows 112 within the automated in-line manufacturing system 100. In some embodiments, the controller 116 may comprise one or more processors. It should be noted that the present disclosure is not limited to any particular processor for performing the processing tasks of the disclosure. The term "processor," as that term is used herein, is intended to denote any machine capable of performing the calculations, or computations, necessary to perform the tasks of the disclosure, and to control the mechanical and electrical devices in the disclosure. The term "processor" is intended to denote any machine that is capable of accepting a structured input and/or of processing the input in accordance with prescribed rules to produce an output, as will be understood by those skilled in the art.

In the embodiment of FIG. 1, the automated in-line manufacturing system 100 further includes one or more clamping, feeding and guide components 124 and one or more cutting components 126 disposed in feed-through positioning with at least one compaction roller 132, configured to deliver a force to adhere the one or more fiber tows 112 to the layup surface 115 of the substrate 114 to form the laminate 110 of the one or more laid up plies 111. The automated in-line manufacturing system 100 may further include a heater 134, a tow guide scoop 136 and a positioning system (not shown) to orient the compaction roller 132 relative to the layup surface 115 of the substrate 114. In one non-limiting example, the in-line manufacturing system 100 may be mounted on a robotic head (not shown) in front of the substrate 114, or mold, such that the one or more fiber tows 112 will adhere to the substrate 114 and pull the fiber feed through the system 100 when the automated in-line manufacturing system 100 moves with respect to the substrate 114. The specific configuration of the composite automated in-line manufacturing system 100 may vary based on the application.

Figure 2:
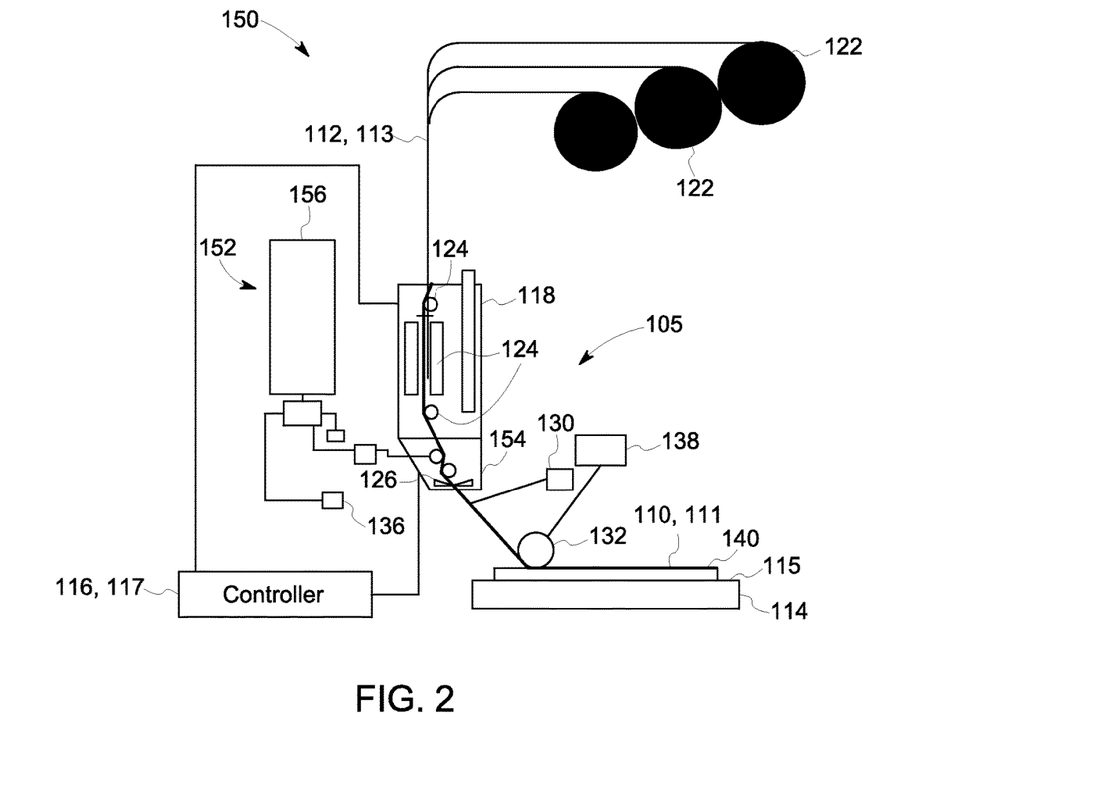
FIG. 2 schematically depicts in side view, an alternate embodiment of an automated in-line manufacturing system for controlling at least one variable during layup of a composite part, in accordance with one or more embodiments shown or described herein.

Referring now to FIG. 2, illustrated is an alternate embodiment of a composite automated in-line manufacturing system, generally referenced 150, including an automated in-line layup system 105 and a controller 116. For the example arrangement shown in FIG. 2, features that are identical to those of FIGS. 1 need not be specifically described, and accordingly like numbers are used to indicate like elements. In the embodiment of FIG. 2, the composite automated in-line manufacturing system 150 may utilize dry fiber tows, and thus further includes an automated resin delivery, deposition and infusion system 152.

Similar to the embodiment of FIG. 1, the composite automated in-line manufacturing system 150 includes a fiber dispensing means 122 for feeding one or more fiber tows 112, where each of the fiber tows 112 is moving at a respective fiber speed. In this particular embodiment, the one or more fiber tows 112 are dry fiber tows. As in the previous embodiment, the fiber dispensing means 118 may be configured to separately feed each of the one or more fiber tows 112, such that the tows 112 can be fed at different rates or at the same rate, depending upon design parameters and in response to the controller 116 and the calculated required layup compensation.

In this particular embodiment, the one or more dry fiber tows 112 move from the clamping, feeding and guide components 124 to a resin delivery, deposition and infusion portion 154 of the automated resin delivery, deposition and infusion system 152. As indicated in FIG. 2, the automated resin delivery, deposition and infusion system 152 includes the resin delivery, deposition and infusion portion 154 comprising a means for delivery, depositing and infusing a resin 156 onto the one or more fiber tows 112. In the illustrated embodiment, the resin delivery, depositing and infusion portion 154 is formed including separate components, but it should be understood that a single component delivery, deposition and infusion portion 154 is anticipated by this disclosure. With regard to the resin 156 and one or more fiber tows 112, the disclosure is not limited to specific resins or fiber types. Additional aspects of an automated resin delivery, deposition and infusion systems and types of resins that may be utilized is further described in U.S. Patent application, entitled, "Resin Delivery, Application and Infusion System and Integrated Layup System and Method of Use", and U.S. patent application Ser. No. 12/889,785, filed by the same assignee, and incorporated herein by this reference.

In addition, in an embodiment where the automated resin delivery, deposition and infusion system 156 is incorporated, any suitable reinforcing material may be infused using the apparatus, systems and methods described herein. Useful fibers to be included in such reinforcing materials, such as tapes, or fabrics, include without limitation, glass fibers, carbon and graphite fibers, basalt fibers, polymeric fibers, including aramide and boron filaments, silica fibers, copper fibers and the like. The fibers may be non-conductive or conductive, depending upon the desired application of the composite fiber. In this particular non-limiting example, the resin 156 is an epoxy resin, and the one or more fiber tows 112 comprise carbon fibers. However, the disclosure is not limited to these specific resins or fiber types.

Similar to the embodiment of FIG. 1, the composite automated in-line manufacturing system 150 further includes a controller 116. The controller 116 is configured to respond to measurement data to provide adjustments to the automated in-line manufacturing system 150, and more particularly the layup program 117, based on calculated required compensation. In an embodiment, measurement data may include one or more samplings of at least one of a weight of the input, or parent material 113, and more particularly the one or more fiber tows 112, and/or a weight of the laminate 110 during fabrication, or part build. The controller 116 is configured to adjust the layup program 117, and thus feed-through of the one or more fiber tows 112, in response to the measurement data, to compensate for a variation from a referenced weight of the input material, and more particularly the one or more fiber tows 112, or the laminate 110, from a predetermined reference weight. More particularly, based on the variance of the samples from the applicable reference, the controller 116, and more particularly the layup program 117 that is controlling the automated in-line manufacturing system 150, is adjusted to compensate for the variation of the one or more tows 112 or the laminate 110 during build. Such adjustments may include, but are not limited to, a change in the number of plies being laid up to form the laminate 110, a change in a length of the one or more fiber tows 112, within the automated in-line manufacturing system 100, and/or control of a flow rate or an amount of the resin 156 through the automated resin delivery, deposition and infusion system 152, using feedback based on measurement data of the one or more samplings.

Similar to the previous embodiment, to provide for the measurement data, the composite automated in-line manufacturing system 150 may include one or more sensors 130 for inline monitoring/sampling at least one of a weight of the input material 113, and more particularly the one or more fiber tows 112, and/or a weight of the laminate 110 during build within the automated in-line manufacturing system 150 during fabrication.

The controller 116 may adjust the layup program 117, to optimize the fabrication of the laminate 110 and thus the composite part 140. As stated, the controller 116 may be configured to adjust the number of plies being laid up in the laminate 110, change a length of the one or more fiber tows 112, and/or control of a flow rate or an amount of the resin 156 through the automated resin delivery, deposition and infusion system 152.

In the embodiment of FIG. 2, the automated in-line manufacturing system 150 is disposed in feed-through positioning with the at least one compaction roller 132 configured to deliver a force to adhere the one or more fiber tows 112 to the layup surface 115 of the substrate 114 to form the laminate 110. A positioning system 138 may be included to orient the compaction roller 132 relative to the layup surface 115 of the substrate 114. The specific configuration of the composite automated in-line manufacturing system 150 may vary based on the application.

Figure 3:
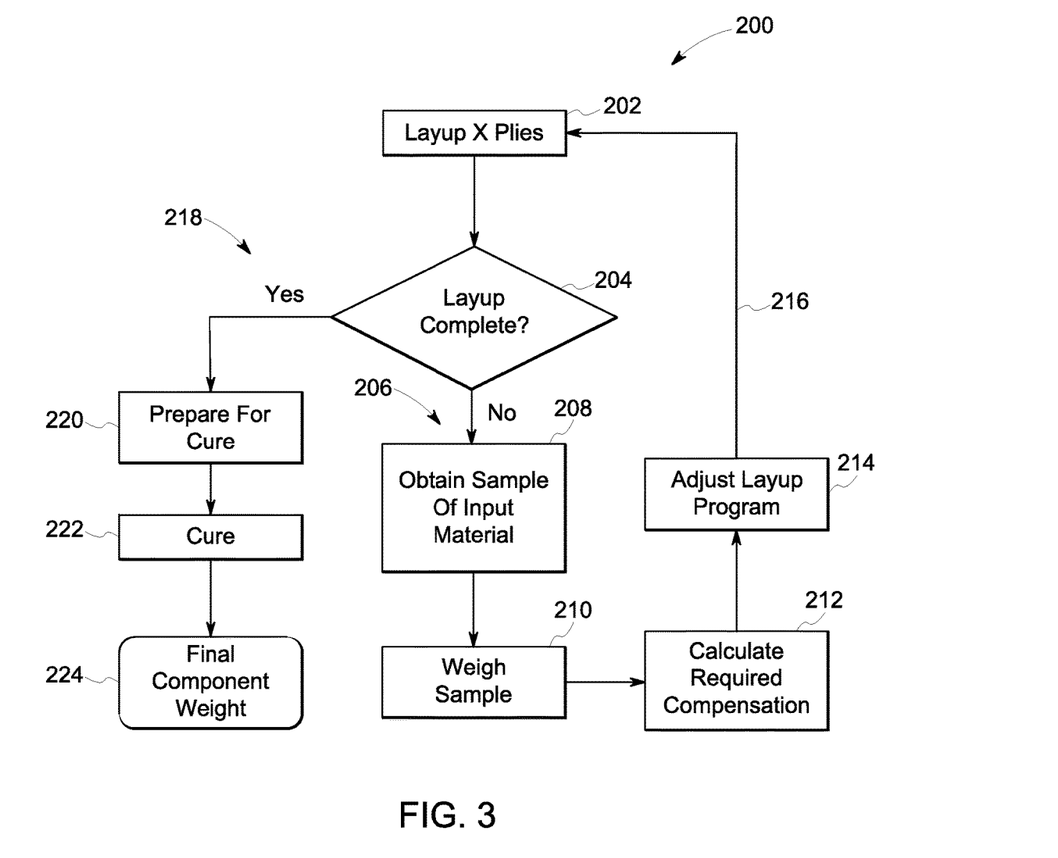
FIG. 3 schematically illustrates a method for controlling at least one variable during layup of a composite part manufactured using the automated in-line manufacturing system of FIG. 1 or FIG. 2, in accordance with one or more embodiments shown or described herein.

Turning now to FIG. 3, illustrated is a method 200 of controlling the thickness and/or weight of a composite part manufactured using an automated in-line manufacturing system, such as the composite part 140 and the automated in-line manufacturing system 100 of FIG. 1 or 150 of FIG. 2. As best illustrated in FIG. 3, initially in a step 202, a number "x" of plies are laid up to form a laminate, wherein each ply comprises one or more fiber tows, such as the one or more fiber tows 112 of FIGS. 1 and 2. The process of laying up the plies includes adhering the one or more fiber tows 112 to a surface of a substrate, such as surface 115 of substrate 114 of FIGS. 1 and 2, to form the composite part, such as the composite part 140 of FIGS. 1 and 2. The automated layup system is configured to receive a feed-through of the one or more fiber tows as an input, or parent, material. Next, in a step 204, a determination is made as to whether the layup of the plies is complete, as indicated at 218, or not complete, as indicated at 206. If not complete, the process of obtaining measurement data is commenced in a step 208 by taking one or more samples from the fiber tows at a known time "$t_x$" and weighing the samples, in a step 210, to obtain the required measurement data. A response to the measurement data is accomplished next by initially calculating a required compensation of the layup process, in a step 212. The step of calculating the required compensation includes taking the measurement data, and more specifically the weight of the input material at time "$t_x$" during the layup process and determining a variation from a reference weight of the input material. Alternatively, the step of calculating the required compensation includes taking the measurement data, and more specifically the weight of the input material at time "$t_x$" during the layup process, and data regarding how much material is laid up at time "$t_x$", to calculate the total weight of the laminate as laid up at time "$t_x$". The calculated weight of the laminate at time "$t_x$" as laid up is compared to a reference weight of the laminate that is required at that stage (time "$t_x$") of the layup according to the component requirements. Next, the layup program is adjusted, in a step 214, in response to the calculated required compensation. More specifically, the method includes responding to the measurement data to compensate for a variation in the weight of the input material or the weight of the laminate that needs to be obtained at that stage (time "$t_x$") of the layup according to the component requirement. The response maybe in the form of adjusting one or more of the layup length of the tows, changing the number of plies, or adjusting the amount of resin delivery when included as a part of the system. Steps 202-214 are repeated, as indicated at 216, in a continuous process until a time in which the layup is determined to be complete, as in step 218. At this time, the completed layup, and more particularly the laminate, is prepared for curing, at step 220 that may include placing the laminate in a vacuum bag. The laminate is next cured, in a step 222, and the final component is weighed, in a step 224.

Figure 4:
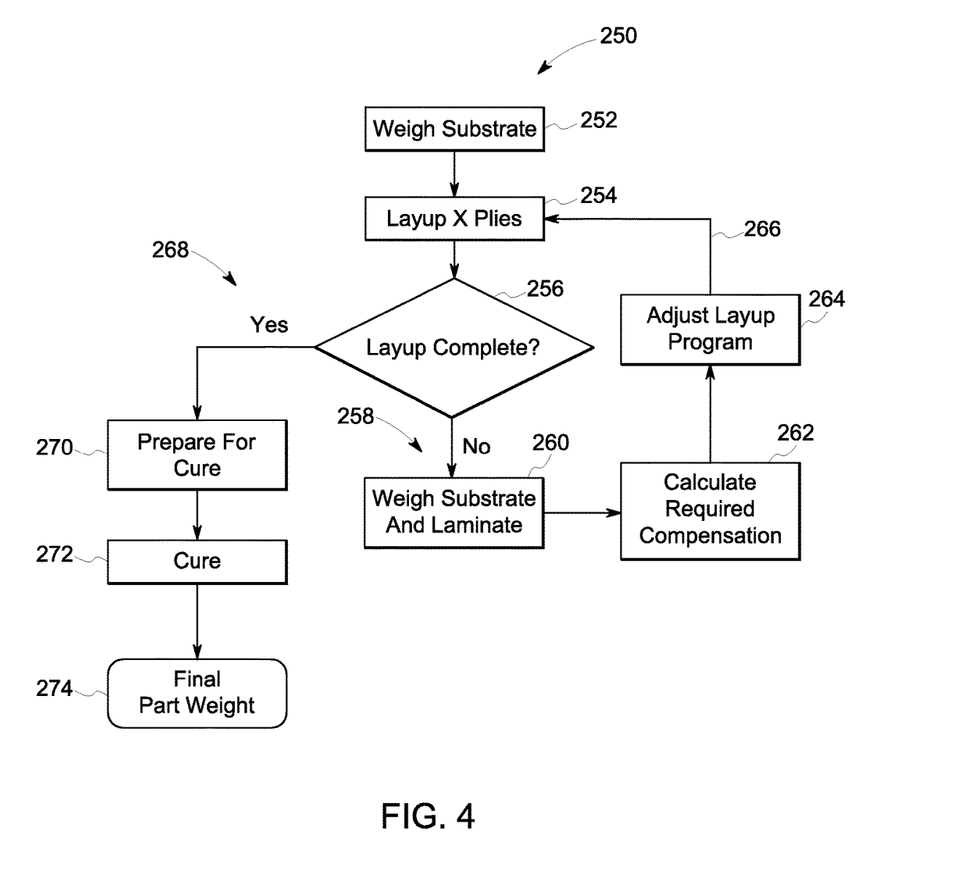
FIG. 4 schematically illustrates an alternate method for controlling at least one variable during layup of a composite part manufactured using the automated in-line manufacturing system of FIG. 1 or FIG. 2, in accordance with one or more embodiments shown or described herein.

Turning now to FIG. 4, illustrated is an alternate method 250 of controlling the thickness and/or weight of a composite part manufactured using an automated in-line manufacturing system, such as the composite part 140 and the automated in-line manufacturing system 100 of FIG. 1 or 150 of FIG. 2. As best illustrated in FIG. 4, initially in a step 252, the substrate is weighed to obtain an initial weight. As used herein, the term "substrate" may be used to indicate a film, or the like, or the mold and/or tool used for fabrication of the composite part, as previously described. Next, in a step 254, a number "x" of plies are laid up, wherein each ply comprises one or more fiber tows, such as the one or more fiber tows 112 of FIGS. 1 and 2. Similar to the previous embodiments of FIGS. 1 and 2, the process of laying up the plies to form the laminate 110 includes adhering the one or more fiber tows 112 to a surface of the substrate, such as surface 115 of substrate 114 of FIGS. 1 and 2, to form the laminate 100 and the final composite part, such as the composite part 140 of FIGS. 1 and 2. The automated layup system is configured to receive a feed-through of the one or more fiber tows as an input material. Next, in a step 256, a determination is made as to whether the layup of the one or more fiber tows, and more particularly the plies forming the laminate, is complete 268 or not complete 258. If not complete, the process of obtaining measurement data is commenced in a step 260 by initially weighing the substrate and weighing the not yet complete layup of plies, or laminate on the substrate. A response to the measurement data is accomplished next by initially calculating a required compensation of the layup process, in a step 262. The step of calculating the required compensation includes taking the measurement data, and more specifically the combined weight of the not yet complete layup of plies (laminate) and the substrate, and subtracting the weight of the substrate from the measured total weight to obtain the laminate weight at a time "$t_x$". The calculated weight of the laminate at time "$t_x$" as laid up is compared to a reference weight of the laminate that is required at that stage (time "$t_x$") of the layup according to the component requirements. Next, the layup program is adjusted, in a step 264, in response to the calculated required compensation. More specifically, the method includes responding to the measurement data to compensate for a variation from the reference weight of the laminate that needs to be obtained at that stage (time "$t_x$") of the layup, according to the component requirement. These responses maybe in the form of one or more of adjusting the layup length of the tows, changing the number of plies, or adjusting the amount of resin delivery when included as a part of the system. Steps 254-264 are repeated, as indicated at 266, in a continuous process until a time in which the layup is determined to be complete, as in step 268. At this time, the completed layup is prepared for curing, at step 270 that may include placing the laminate in a vacuum bag. The laminate is next cured, in a step 272, and the final component is weighed, in a step 274.

Figure 5:
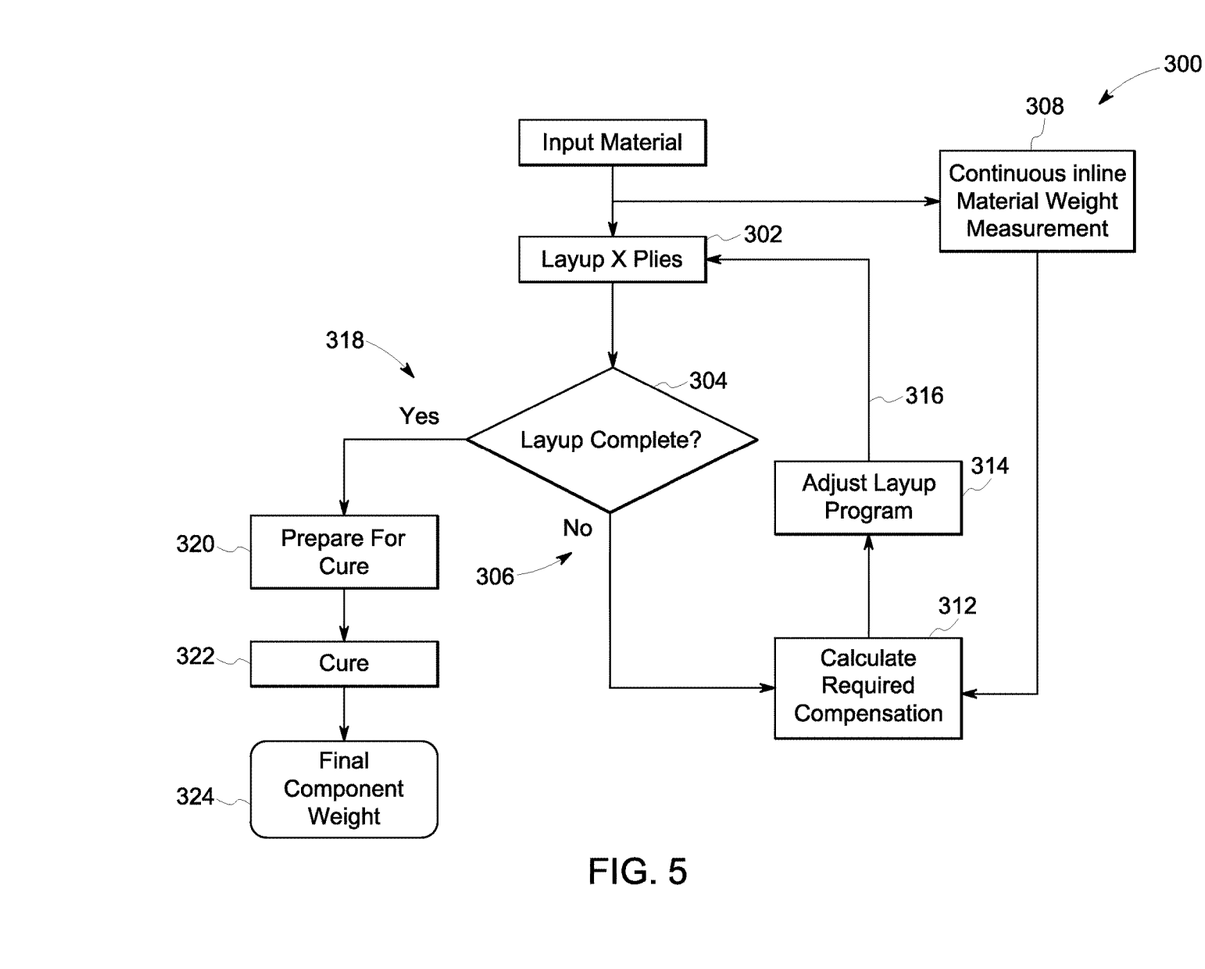
FIG. 5 schematically illustrates another alternate method for controlling at least one variable during layup of a composite part manufactured using the automated in-line manufacturing system of FIG. 1 or FIG. 2, in accordance with one or more embodiments shown or described herein.

Turning now to FIG. 5, illustrated is yet another alternate embodiment of a method 300 of controlling the thickness and/or weight of a composite part manufactured using an automated in-line manufacturing system, such as the composite part 140 and the automated in-line manufacturing system 100 of FIG. 1 or 150 of FIG. 2. As best illustrated in FIG. 5, initially in a step 302, a number "x" of plies are laid up, wherein each ply comprises one or more fiber tows, such as the one or more fiber tows 112 of FIGS. 1 and 2. The process of laying up the plies includes adhering the one or more fiber tows 112 to a surface of a substrate, such as surface 115 of substrate 114 of FIGS. 1 and 2, to form the laminate and thus final composite part, such as the laminate 110 and composite part 140 of FIGS. 1 and 2. The automated layup system is configured to receive a feed-through of the one or more fiber tows as an input, or parent, material. Next, in a step 304, a determination is made as to whether the layup of the plies is complete, as indicated at 318, or not complete, as indicated at 306. During the process of laying up the input material, continuous inline measurement data is obtained of the input material, prior to layup, as indicated at step 308. The continuously obtained measurement data provides for calculations to be performed, in a step 312, to provide for continuous compensation of the layup process 300. More specifically, the step of calculating the required compensation includes taking the continuously obtained measurement data, and more specifically the weight of the input material prior to the layup process, and identifying variations from a reference weight of the input material. Next, the layup program is continually adjusted during the layup process, in a step 314, in response to the calculated required compensation. More specifically, the method includes responding to the measurement data to compensate for a variation in the weight of the input material from the reference weight of the input material as required by the component requirements. These responses maybe in the form of one or more of adjusting the layup length of the tows, changing the number of plies, or adjusting the amount of resin delivery when included as a part of the system. Steps 302-314 are repeated, as indicated at 316, in a continuous process until a time in which the layup is determined to be complete, as in step 318. At this time, the completed layup is prepared for curing, at step 320 that may include placing the layup plies in a vacuum bag. The completed layup is next cured, in a step 322, and the final component is weighed, in a step 324.

Beneficially, by integrating the ability to adapt the layup process to the measured material properties, and more particularly adapt one or more variables during the layup process with an automated layup system, advanced composite structures can be fabricated, despite having complex shapes, without requiring additional manufacturing processes and steps to achieve near-net shape. The disclosed composite automated in-line manufacturing system integrates the ability to build a part with reduced variation in thickness and weight distribution as compared with the input material. The automated process of the present disclosure thus providing fabrication of complex composite structures with improved control and at lower cost than conventional fiber placement systems. The process advantageously provides automation and the determination of required adjustments that can be embedded in the automated fiber placement program. The composite automated in-line manufacturing system includes sufficient flexibility to accommodate multiple algorithms for adjustments responding to sample measurements. Commercially, by integrating the ability adapt the layup to the measured material properties, during part fabrication with the automated layup system, full automation is obtained resulting in a reduction in cycle time and cost. The method and system as disclosed herein enables one to build a part with reduced variation in thickness and weight distribution as compared with the input material.

Although only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. An automated in-line manufacturing system for controlling at least one variable during layup of a composite part using automated fiber placement comprising:
    an automated layup system configured to receive a feed-through of one or more fiber tows as an input material and provide layup of the one or more fiber tows to form a laminate of one or more laid up plies;
    one or more sensors to obtain measurement data in one or more samplings during the layup of the one or more fiber tows; and
    a controller configured to respond to the measurement data obtained in the one or more samplings and adjust the feed-through of the one or more fiber tows during the current layup, including adjusting one or more of a length of the one or more fiber tows and a number of plies being laid up, to compensate for a variation in the current layup, as evidenced by the measurement data obtained during the layup in the one or more samplings, from one or more of a reference weight of the input material and a reference weight of the laminate.

2. The automated in-line manufacturing system of claim 1, wherein the measurement data includes at least one of a weight of the input material and a weight of the laminate.

3. The automated in-line manufacturing system of claim 1, wherein the system further comprises an automated resin delivery deposition and infusion system, the controller further configured to control the flow rate of a resin through the automated resin delivery, deposition and infusion system using feedback based on measurement data obtained in the one or more samplings.

4. The automated in-line manufacturing system of claim 1, wherein the automated layup system further comprises at least one spool of a resin infused fiber tape as the input material.

5. The automated in-line manufacturing system of claim 1, wherein the automated layup system further comprises at least one spool of a resin infused composite fiber as the input material.

6. The automated in-line manufacturing system of claim 1, wherein the automated layup system further comprises at least one spool of a reinforcing material comprising one or more of glass fibers, carbon fibers, graphite fibers, aramid fibers, basalt fibers, polymeric fibers, silica fibers and copper fibers as the input material.

7. An automated in-line manufacturing system for controlling at least one of a thickness and a weight of a composite part manufactured with the automated in-line manufacturing system, the system comprising:
    an automated layup system configured to receive a feed-through of one or more fiber tows as an input material and provide layup of the one or more fiber tows to form a laminate of one or more laid up plies;
    one or more sensors to obtain measurement data in one or more samplings during the layup of the one or more fiber tows; and
    a controller configured to adjust at least one of a fiber tow length and a change in a number of plies being laid up using feedback based on the measurement data obtained in the one or more samplings to compensate for a variation in the current layup, as evidenced by the measurement data obtained during the layup in the one or more samplings from one or more of a reference weight of the input material and a reference weight of the laminate.

8. The automated in-line manufacturing system of claim 7, wherein the system further comprises an automated resin delivery deposition and infusion system, the controller further configured to control the flow rate of a resin through the automated resin delivery, deposition and infusion system using feedback based on measurement data of the one or more samplings.

9. The automated in-line manufacturing system of claim 7, wherein the automated layup system further comprises at least one spool of prepreg tows as the input material.

10. A method for controlling the thickness and weight of a composite part manufactured using an automated in-line manufacturing system, the method comprising:

(a) laying up one or more fiber tows using an automated layup system to form a laminate of one or more laid up plies, the laying up process including adhering the one or more fiber tows to a surface of a substrate to form the laminate, the automated layup system configured to receive a feed-through of the one or more fiber tows as an input material;

(b) obtaining measurement data in one or more samplings during the laying up of the one or more fiber tows;

(c) responding to the measurement data obtained in the one or more samplings to adjust the feed-through of the one or more fiber tows during the current layup, including adjusting one or more of a fiber tow length and a change in a number of plies being laid up to compensate for a variation in the current layup, as evidenced by the measurement data obtained during the layup in the one or more samplings from one or more of a reference weight of the input material and a reference weight of the laminate; and (d) repeating steps (a)-(c) until layup of the one or more fiber tows is complete.

11. The method of claim 10, further comprising:

(e) determining the layup of the one or more fiber tows is complete;

(f) curing the laminate; and (g) obtaining a weight of the completed composite part.

12. The method of claim 10, wherein the step of obtaining measurement data comprises obtaining a weight of a sampling of the input material during the laying up of the one or more fiber tows.

13. The method of claim 10, wherein the step of obtaining measurement data comprises obtaining a weight of a sampling of the input material at a given time during the laying up of the one or more fiber tows and determining a weight of the laminate based on the amount of input material laid up at the given time.

14. The method of claim 10, wherein the step of obtaining measurement data comprises obtaining a weight of the laminate during the laying up of the one or more fiber tows.

15. The method of claim 14, wherein the step of obtaining a weight of the laminate during the laying up of the one or more fiber tows comprises obtaining a weight of the substrate and obtaining a combined weight of the laminate and substrate during the laying up of the one or more fiber tows to calculate the weight of the laminate.

16. The method of claim 10, wherein the step of obtaining measurement data comprises weighing a continuous sampling of the input material during the laying up of the one or more fiber tows.

17. The method of claim 10, wherein the step of responding to the measurement data to adjust the layup of the one or more fiber tows includes calculating a required compensation of the laying up of the one or more fiber tows.

18. The method of claim 10, wherein the step of obtaining measurement data includes obtaining measurement data from one or more sensors.

* * * * *